(12) United States Patent
Yde et al.

(10) Patent No.: US 8,501,456 B2
(45) Date of Patent: Aug. 6, 2013

(54) METHOD FOR MAKING LACTIC ACID BACTERIA COMPOSITION

(75) Inventors: Birgitte Yde, Farum (DK); Susanne Abrahamsen, Karlslunde (DK)

(73) Assignee: CHR. Hansen A/S, Hoersholm (DK)

( * ) Notice: Subject to any disclaimer, the term of this patent is extended or adjusted under 35 U.S.C. 154(b) by 0 days.

(21) Appl. No.: 13/201,533

(22) PCT Filed: Feb. 18, 2010

(86) PCT No.: PCT/EP2010/052017
§ 371 (c)(1),
(2), (4) Date: Sep. 19, 2011

(87) PCT Pub. No.: WO2010/094727
PCT Pub. Date: Aug. 26, 2010

(65) Prior Publication Data
US 2012/0003721 A1    Jan. 5, 2012

(30) Foreign Application Priority Data
Feb. 23, 2009 (EP) ..................................... 09153419

(51) Int. Cl.
*C12N 1/20* (2006.01)
*C12N 1/12* (2006.01)
(52) U.S. Cl.
USPC .................. 435/252.9; 435/252.1; 435/253.4
(58) Field of Classification Search
None
See application file for complete search history.

(56) References Cited

U.S. PATENT DOCUMENTS

| 3,897,307 A | 7/1975 | Porubcan et al. |
| 4,243,687 A * | 1/1981 | Kline .............................. 426/62 |
| 6,787,348 B1 * | 9/2004 | Kringelum et al. ......... 435/252.9 |
| 2006/0204484 A1 * | 9/2006 | Bisgaard-Frantzen et al. ......................... 424/93.45 |

FOREIGN PATENT DOCUMENTS

| CN | 101230323 A | 7/2008 |
| EP | 1 038 951 A1 | 9/2000 |
| WO | WO 00/07571 | 2/2000 |

OTHER PUBLICATIONS

Kurtmann et al. Cryobiology, vol. 58, 2009, pp. 175-180 (shows online publication date of Dec. 2008).*
International Search Report PCT/EP2010/052017 dated Apr. 28, 2010.
Tateki Hayashi et al., "Red Pigment Formation by the Reaction of Oxidized Ascorbic Acid and Protein in a Food Model System of Low Moisture Content", Agric. Biol. Chem., 49 (11) 3139-3144, 1985.
Lone Kurtmann et al., "Storage Stability of Freeze-Dried *Lactobacillus acidophilus* (La-5) in Relation to Water Activity and Presence of Oxygen and Ascorbate", Cryobiology 2009, doi:10.1016/j.cryobiol. 2008.12.001, 6 pgs.

* cited by examiner

*Primary Examiner* — Chris R Tate
*Assistant Examiner* — Douglas F White
(74) *Attorney, Agent, or Firm* — Foley & Lardner LLP

(57) ABSTRACT

A method for making at least 2 kg (dry weight) of a lactic acid bacteria composition formulated with from 1% to 50% of ascorbate or ascorbic acid (w/w–dry matter) as antioxidant, wherein the pH is controlled so $3 \leq pH \leq 8$ during at least the majority of the fermentation process by addition of a base not comprising $NH_3$ (ammonia).

15 Claims, 3 Drawing Sheets

Sodium ascorbate          Ascorbic acid

BB-12® formulated with sodium ascorbate and stored at 30° C/30% RH

La-5® formulated with sodium ascorbate and stored at 30° C/30% RH

US 8,501,456 B2

METHOD FOR MAKING LACTIC ACID BACTERIA COMPOSITION

FIELD OF THE INVENTION

The present invention relates to a method for making at least 2 kg (dry weight) of a lactic acid bacteria composition formulated with from 1% to 50% of ascorbate or ascorbic acid (w/w–dry matter) as antioxidant, wherein the pH is controlled so $3 \leq pH \leq 8$ during at least the majority of the fermentation process by addition of a base not comprising $NH_3$ (ammonia).

BACKGROUND ART

Lactic acid bacteria relate to a group of Gram-positive, non-sporing bacteria, which carry out a lactic acid fermentation of sugars.

Lactic acid bacteria are commercially widely used for instance in the preparation of different food products such as e.g. yogurts.

Further, many lactic acid bacteria are probiotics—i.e. live microorganisms which when administered in adequate amounts confer a health benefit on the host (e.g. a human).

A lactic acid bacteria product is commercially often sold as a dried composition—e.g. a freeze dried composition. The dried composition may e.g. be dried pellets or a tablet (e.g. made from milled dried pellets).

Lactic acid bacteria (e.g. dried) to be used for human or animal consumption are frequently formulated with ascorbic acid or ascorbate such as e.g. sodium ascorbate as antioxidant—sodium ascorbate e.g. improves the storage stability of the lactic acid bacteria product.

Figure 1:
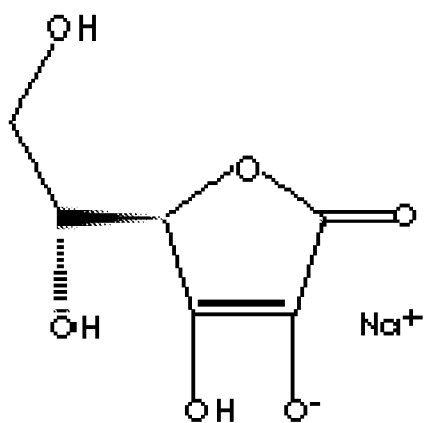
Figure 1:
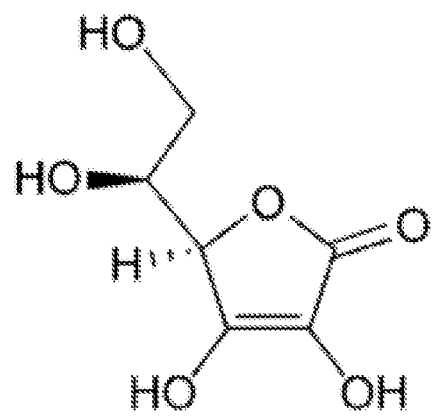

Sodium ascorbate is a salt of ascorbic acid (vitamin C) and it has the common E-number E301 (see EU food additive legislation). The structures of sodium ascorbate and ascorbic acid are shown in FIG. 1 herein.

The article—L. Kurtmann et al., "Storage stability of freeze-dried *Lactobacillus acidophilus* (La-5) in relation to water activity and presence of oxygen and ascorbate"; Cryobiology (2009), doi:10.1016/j.cryobiol.2008.12.001—was published on the Internet in December 2008.

The L. Kurtmann et al article describes that when sodium ascorbate was present a pink/red color was observed on the surface of dried *Lactobacillus acidophilus* compositions/samples during storage (see e.g. the abstract).

Such a pink/red color is unwanted—for instance many consumers do not like such a pink/red color since it may give an un-healthy "look" of the dried lactic acid bacteria product.

During fermentation lactic acid bacteria makes lactic acid—accordingly in order for not getting a too low pH during production the pH is controlled during fermentation by addition of a base.

Generally, the pH is controlled in order to have a $3 \leq pH \leq 8$ during at least the majority of the fermentation process, since lactic acid bacteria generally do not grow properly at pH below 3.

In the L. Kurtmann et al article *L. acidophilus* (La-5®) from Chr. Hansen A/S was used. In the article it is generically stated that pH was controlled during fermentation (see Material and methods). No mention is made about how the pH control was carried out.

Use of $NH_3$ as base is very normal for commercial industrial relevant production of lactic acid bacteria products in industry—in fact it may be considered as a "standard".

Page 179, right column of the L. Kurtmann article discussed above indicates that amino groups from the bacterial cells or from fermentation residues could be involved in the creation of the unwanted pink/red color—the article reads "a red compound is formed when ascorbic acid is oxidized to dehydroascorbic acid and reacts with amino groups forming the pigment".

As further discussed below—in fact one may say that this disclosed theory of the L. Kurtmann article TEACHES AWAY from the present invention (i.e. NOT using a base comprising $NH_3$).

EP-A-1038951 (Nestle [CH]) discloses a media for cultivating bacteria, the media comprising ascorbic acid as an antioxidant and buffers like $Na_2CO_3$, $KH_2PO_4$ (see page 3, claims 3 and 4).

In [0026] it is said that e.g. ascorbic acid is provided simply as an example of a suitable antioxidant comprises in the fermentation MEDIUM.

Said in other words, EP-A-1038951 do not directly and unambiguously disclose a method for making bacteria, wherein ascorbic acid is added to the harvested bacteria concentrate—i.e. as discussed below, EP-A-1038951 does not explicitly disclose step (iii) of first aspect (claim 1) of the present invention as described herein.

SUMMARY OF THE INVENTION

The problem to be solved by the present invention is to provide a new method for producing a lactic acid bacteria composition (e.g. dried) formulated with ascorbate or ascorbic acid as antioxidant, wherein the composition is not developing a significant pink/red color during storage of the composition.

The inventors identified that unwanted pink/red color development is relevant for different lactic acid bacteria cultures formulated with sodium ascorbate—i.e. not only for the *Lactobacillus acidophilus* (La-5®) composition/sample analyzed in the article of L. Kurtmann.

As shown in working examples herein—the pink/red color was also present in other commercial relevant cultures such as the *Lactobacillus rhamnosus* (LGG®), *Streptococcus thermophilus* (TH-4™) and *Bifidobacterium animalis* (BB-12®) cultures.

By investigating this further, the present inventors identified that $NH_3$ had been used as base for the fermentation pH control for all the analyzed La-5®, LGG®, TH-4™ and BB-12® compositions.

Working further with it—the present inventors identified that by using NaOH as base in stead of $NH_3$—it was surprisingly possible to produce dried La-5®, LGG®, TH-4™ and BB-12® compositions formulated with sodium ascorbate, wherein the compositions were NOT developing a significant pink/red color during storage of the compositions—see working examples herein for further details.

Accordingly, the essence of the invention may be seen in NOT using a base comprising $NH_3$ (ammonia).

Without being limited to theory, it is believed that the pink/red color problem in relation to use of $NH_3$ may have following theoretical explanation.

Ammonia ($NH_3$) is in equilibrium with ammonium ($NH_4^+$). The equilibrium has a pKa of 9.25 meaning that at pH <9.25 the majority will be present as ammonium ($NH_4^+$)—i.e. positively charged at the pH the culture is adjusted to in step (i) of first aspect of the invention (see below).

The pKa for the two —OH groups in ascorbic acid is 4.17 and 11.6 respectively. This means that the —OH group with the pKa of 4.17 is deprotonated and there will be a negative charge (electron rich) point in the ascorbate molecule. In FIG. 1 herein is shown the structure of sodium ascorbate and ascorbic acid. It is evident that this is most pronounced at pH above 4—however due the equilibrium effects it will—as known to the skilled person also be relevant for pH above 3.

Without going into too many details—the essence of the theory is that the positively charged $NH_3$ (i.e. $NH_4^+$) "attack" the negatively charged (electron rich) point in the ascorbate molecule and this initiates a chain of reactions which at the end result in compounds giving/developing the unwanted pink/red color during storage.

As evident to the skilled person—NaOH does not have a similar to $NH_4^+$ positively charged reactive group and this is—according to theory—an essential reason for that the pink/red color is not seen when NaOH is used as base.

Page 179, right column of the L. Kurtmann article discussed above indicates that amino groups from the bacterial cells or from fermentation residues could be involved in the creation of the unwanted pink/red color—the article reads "a red compound is formed when ascorbic acid is oxidized to dehydroascorbic acid and reacts with amino groups forming the pigment".

In fact one may say that this disclosed theory of the L. Kurtmann article TEACHES AWAY from the present invention (i.e. NOT using a base comprising $NH_3$).

In short, one may say that the L. Kurtmann theory is based on other prior art indications that it could be amino groups that could be involved in the creation of the unwanted pink/red color.

Overall, the amino group based theory in the prior art may be summarized as the prior art refers to that the amino group is attacking the carbonyl carbon of dehydroascorbic acid (DHA)—it is here important to note that the carbonyl carbon has a partial positive charge (i.e. an $\sigma+$ charge) so that the lonely electron pair from the amino group can attack the partial positively charged carbon.

As discussed above—the ammonia has a pKa of 9.25 meaning that at pH<9.25 the majority will be present as ammonium ($NH_4^+$)—i.e. positively charged at the pH the culture is adjusted to in step (i) of first aspect of the invention.

As evident to the skilled person—the positive ammonia can NOT attack the partial positively charged carbonyl carbon of DHA meaning that ammonia can NOT be involved in the creation of the unwanted red/pink color by use of the "mechanism" of the theory described in the L. Kurtmann article.

Said in other words—one may say that the amino group related theory/mechanism described in the L. Kurtmann article TEACHES AWAY from the present invention, since one would objectively derive/understand from this L. Kurtmann theory/mechanism that ammonia (i.e. $NH_4^+$ at herein relevant pH) should NOT be "dangerous" (i.e. $NH_4^+$ should NOT be involved in the creation of the unwanted red/pink color).

As known to the skilled person—one may routinely identify other bases than NaOH that is not comprising $NH_3$ (ammonia) such as e.g. KOH, $Na_2CO_3$.

Further, as evident to the skilled person the theory above is not only relevant for sodium ascorbate but generally for any relevant ascorbate or ascorbic acid.

As discussed above, the pink/red color is unwanted because for instance many consumers do not like such a pink/red color since it may give an un-healthy "look" of the lactic acid bacteria product.

Accordingly, the present invention is highly relevant for commercially relevant production of lactic acid bacteria composition, which is normally produced in industrial relevant large scale.

Accordingly, a first aspect of the invention relates to a method for making at least 2 kg (dry weight) of a lactic acid bacteria composition formulated with from 1% to 50% of ascorbate or ascorbic acid (w/w–dry matter) as antioxidant wherein the method comprises the following steps:

(i): fermenting the lactic acid bacteria—in a fermentor (bioreactor) comprising at least 100 I fermentation medium—under suitable conditions and wherein the pH is controlled so $3 \leq pH \leq 8$ during at least the majority of the fermentation process by addition of a base not comprising $NH_3$ ammonial;

(ii): harvesting of the lactic acid bacteria to get lactic acid bacteria concentrate;

(iii): adding ascorbate or ascorbic acid to the lactic acid bacteria concentrate; and (iv): processing in a suitable way the ascorbate or ascorbic acid containing concentrate of step (iii) to get the lactic acid bacteria composition formulated with from 1% to 50% of ascorbate or ascorbic acid (w/w–dry matter) as antioxidant.

As understood by the skilled person one does not remove all added base in harvesting step (ii). Accordingly, relevant amount of the added base is present in the bacteria concentrate and therefore also present when e.g. sodium ascorbate is added to the concentrate in step (iii).

As discussed above, the essence of the invention may be seen in NOT using a base comprising $NH_3$ (ammonia)—i.e. the "addition of a base not comprising $NH_3$ (ammonia)" in step (i).

All the other steps of the method of the first aspect may essentially be seen as routine steps made according to the prior art.

Routine steps—such as e.g. fermenting under suitable conditions of step (i)—may not be discussed in further details herein since the skilled person routinely knows how to perform such prior art routine steps.

DRAWINGS

FIG. 1: The structures of sodium ascorbate and ascorbic acid.

Figure 2:
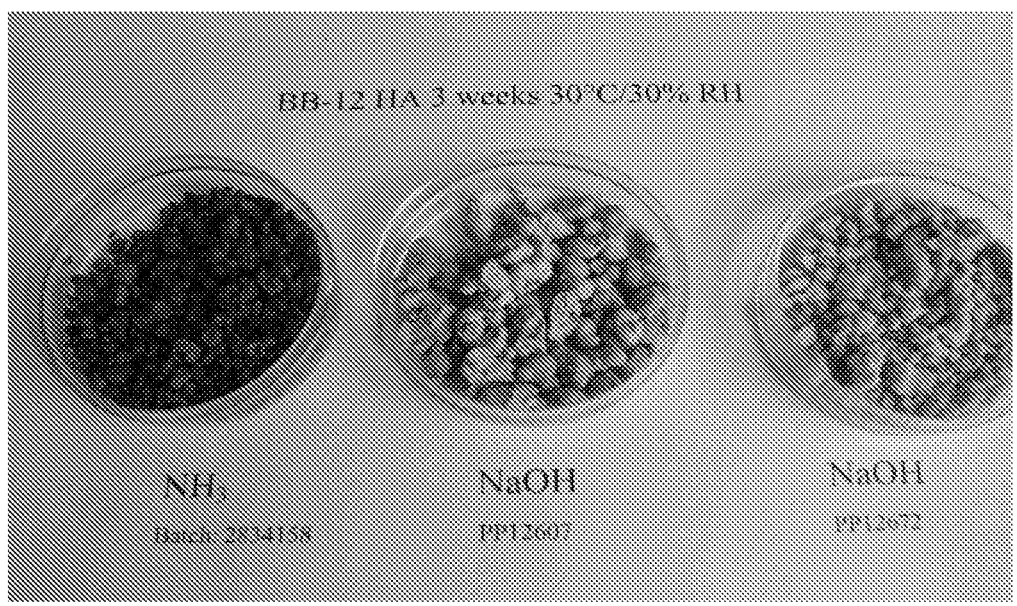

FIG. 2: The picture in FIG. 2 shows the differences in color of a BB-12® batch produced in production where $NH_3$ is used for pH adjustment during fermentation and two batches produced in Pilot Plant where NaOH is used for pH adjustment during fermentation.

Figure 3:
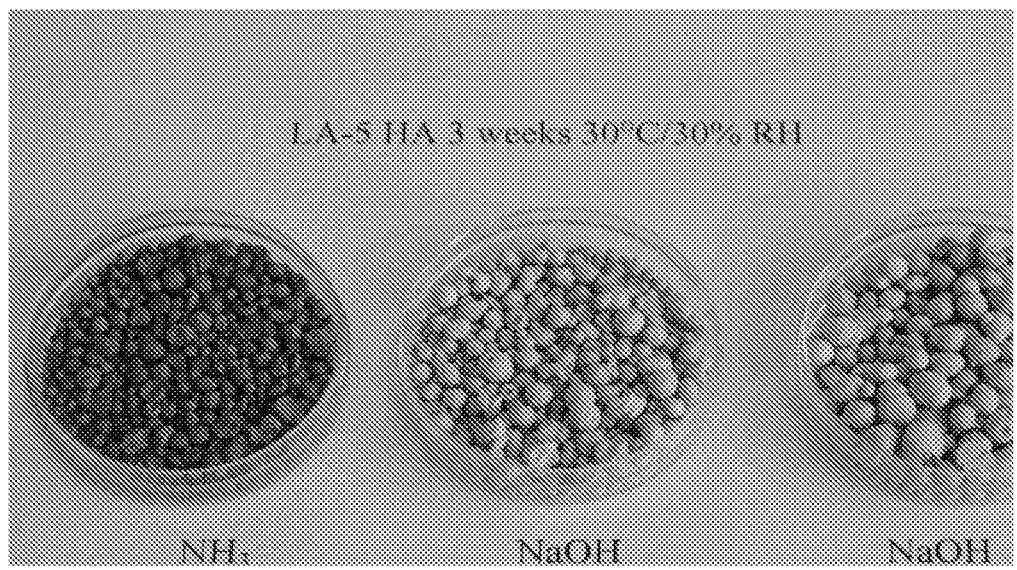

FIG. 3: The picture in FIG. 3 shows the same—as in FIG. 2—for La-5®.

DETAILED DESCRIPTION OF THE INVENTION

Lactic Acid Bacteria

As discussed above, the term "lactic acid bacteria" relates to a group of Gram-positive, non-sporing bacteria, which carry out a lactic acid fermentation of sugars.

Preferably, the lactic acid bacteria are lactic acid bacteria selected from the group consisting of:

lactic acid bacteria belonging to genus *Lactobacillus*, such as *Lactobacillus helveticus, Lactobacillus delbruekii* subsp. *bulgaricus, Lactobacillus fermentum, Lactobacillus salivarius* or *Lactobacillus rhamnosus;* lactic acid bacteria belonging to genus *Lactococcus*, such as *Lactococcus lactis;* lactic acid bacteria belonging to genus *Streptococcus*, such as *Streptococcus thermophilus;* lactic acid bacteria belonging to genus *Leuconostoc*, such as *Leuconostoc lactis;* lactic acid bacteria belonging to genus *Bifidobacterium*, such as *Bifidobacterium longum, bifidobacterium animalis*, or *Bifidobacterium breve*;
lactic acid bacteria belonging to genus *Propioni* bacteria;
lactic acid bacteria belonging to genus *Enterococcus*, such as *Enterococcus faecum*; and
lactic acid bacteria belonging to genus *Pediococcus*.

Some literature theoretically discusses if Bifidobacterium is a "real" lactic acid bacterium. In the present context a Bifidobacterium is a lactic acid bacterium.

Within the lactic acid bacteria group above it is preferred that at least one lactic acid bacterium is selected from the group consisting of:
lactic acid bacteria belonging to genus *Lactobacillus*;
lactic acid bacteria belonging to genus *Streptococcus*;
lactic acid bacteria belonging to genus *Bifidobacterium*; and
lactic acid bacteria belonging to genus *Lactococcus*.

Even more preferably, the lactic acid bacteria are lactic acid bacteria selected from the group consisting of:
*Lactobacillus acidophilus, Lactobacillus rhamnosus, Streptococcus thermophilus* and *Bifidobacterium animalis*.

Most preferably, the lactic acid bacteria are lactic acid bacteria selected from the group consisting of:
*Lactobacillus acidophilus* strain with deposit accession number DSM 13241;
*Bifidobacterium animalis* strain with deposit accession number DSM 15954; and
*Streptococcus thermophilus* strain with deposit accession number DSM 15957.

The DSM 13241 strain may herein be termed La-5®, the DSM 15954 strain may herein be termed BB-12® and the DSM 15957 strain may herein be termed TH-4™.

Ascorbic Acid or Ascorbate

As known—ascorbate is a salt of ascorbic acid.

Herein it may be preferred to use sodium ascorbate as a suitable ascorbate.

Examples of other suitable salts of ascorbic acid (ascorbate) include calcium ascorbate, magnesium ascorbate or 2-phosphate trisodium ascorbate.

Use of ascorbic acid may also be relevant—however due to its acidic effect one needs to take this into account for relevant pH adjustment.

Lactic Acid Bacteria Composition

The lactic acid bacteria composition may comprise one single strain (e.g. *Lactobacillus acidophilus* (La-5®)) or it may comprise a mixture of different strains. It may also comprise not lactic acid bacteria such as e.g. yeast.

The weight of the composition is preferably at least 5 kg (dry weight), more preferably at least 15 kg (dry weight) and most preferably at least 50 kg (dry weight).

As understood by the skilled person—a higher weight of the composition is related to a bigger large scale production that may be advantageous for obvious reasons.

Commercially, is many times used freeze-drying. Accordingly, if drying is used in step (iv) of first aspect it may be freeze drying to get a freeze dried lactic acid bacteria composition.

As discussed above, the lactic acid bacteria composition is formulated with from 1% to 50% of ascorbate or ascorbic acid (w/w–dry matter).

The term "w/w–dry matter" is understood by the skilled person to mean weight based on dry matter of the composition.

For instance if the lactic acid bacteria composition is a frozen composition—e.g. 10% of ascorbate or ascorbic acid (w/w–dry matter) shall be understood as one dries e.g. a sample of the composition and then measures that there is 10% ascorbate or ascorbic acid as dry matter of the composition.

Many times the lactic acid bacteria composition is formulated with from 2% to 24% of ascorbate or ascorbic acid (w/w–dry matter) or it is formulated with from 5% to 15% of ascorbate or ascorbic acid (w/w–dry matter).

As evident to the skilled person, the amount of added e.g. sodium ascorbate in step (iii) of first aspect will determine the amount of e.g. sodium ascorbate (w/w–dry matter) in the lactic acid bacteria composition after e.g. drying of step (iv).

As evident to the skilled person one may add other relevant compounds to the concentrate in step (iii) of first aspect.

For instance, if freeze drying is used in step (iv) there is normally added so-called cryoprotectant in step (iii).

A cryoprotectant is a substance that is used to protect biological tissue from freezing damage (damage due to ice formation) and examples of a suitable cryoprotectant are e.g. sucrose, maltodextrin, trehalose or glycerol.

Fermenting—Step (i) of First Aspect

Depending on how big one makes the large scale production—the fermentor (bioreactor) may comprise at least 500 l fermentation medium or at least 10000 l fermentation medium.

As discussed above, the pH is controlled so $3 \leq pH \leq 8$ during at least the majority of the fermentation process by addition of a base not comprising $NH_3$ (ammonia).

The pH is controlled in order to have a $3 \leq pH \leq 8$ during at least the majority of the fermentation process, since lactic acid bacteria generally do not grow properly at pH below 3.

Defending on the specific type of lactic acid bacteria—the pH may be controlled so $4 \leq pH \leq 7$.

Generally speaking, the skilled person knows how to control pH during fermentation by proper addition of suitable amounts of base.

As evident to the skilled person in the present context—the term "majority" in step (i) should be understood as that the pH may some times for relatively short times e.g. get below 3—for instance just before extra amount of base is added in case the base is not added continuously.

Base Not Comprising $NH_3$ (Ammonia)

As discussed above—in working examples herein is used NaOH as a good example of a suitable base not comprising NH3 (ammonia).

As know to the skilled person—suitable examples may be at least one base selected from the group of bases consisting of: $NaOH$, $KOH$, $Na_2CO_3$, $Na_2S$ and $Na_2O$.

Within the list above NaOH or KOH are generally most preferred.

Steps (ii) to (iv) of First Aspect

As discussed above, all the steps (ii) to (iv) of the method of the first aspect may essentially be seen as routine steps made according to the prior art.

For instance, as known to the skilled person harvesting of the lactic acid bacteria to get lactic acid bacteria concentrate (step (ii)) may be by centrifugation. Harvesting may also be by ultra-filtration.

For instance, as known to the skilled person one may add the e.g. sodium ascorbate to the lactic acid bacteria concentrate (step (iii)) by e.g. dissolving dry sodium ascorbate in water before it is added to the concentrate. Alternatively, one may add dry sodium ascorbate "directly" into the concentrate.

With respect to step (iv) the specific way of processing will of course depend on the application.

For instance, if one wants a dried lactic acid bacteria composition then the processing in step (iv) is drying.

If one wants a frozen lactic acid bacteria composition then the processing in step (iv) is freezing.

Alternatively, if one want a liquid lactic acid bacteria composition then one actually does not need to do any further processing after step (iii).

EXAMPLES

Example 1

Color Measurements

The pink/red color measurement was done as described in the article discussed herein of L. Kurtmann.

As explains on page 2 of the article the color measurements are done in the following way:

The surface color of the dried cultures was measured using the CIELAB color system with the L*, a* and b* coordinates and measured by a Tristimulus Colorimeter (Minolta Chroma Meter CR-300, Osaka, Japan). In this study the color changes were expressed by the b* value, which measures yellowness (+) or blueness (−), where an increase in the b* value reflects a change in color towards yellow and brown, and the a* value, which measures the redness (+) or greenness (−). The values were determined as the mean of three measurements each at 10 different places on the surface of the dried bacteria sample.

Example 2

Exchange of $NH_3$ with NaOH for pH Adjustment During Fermentation

Strains—commercially available from Chr. Hansen A/S:
Lactobacillus acidophilus (La-5®);
Lactobacillus rhamnosus (LGG®)
Bifidobacterium animalis (BB-12®).
Streptococcus thermophilus (TH-4™)
Methods:

For all 3 strains were made pilot scale production in accordance with the method of the first aspect herein.

For each strain there were in one production used NaOH to control pH during the fermentation (step (i) of first aspect) and as a control/reference was in another production used $NH_3$ to control pH. Everything else—e.g. the amount of added sodium ascorbate in step (iii)—were 100% identical in the productions.

All produced lactic acid bacteria compositions comprised around 10% of sodium ascorbate (w/—dry matter) as antioxidant in the dry product.

After freeze drying (step (iv))—The color change of freeze dried lactic acid bacteria compositions produced by respectively NaOH and $NH_3$ stored at 30° C./30% relative humidity (RH) was followed.

The color of all the products was measured with a Minolta colorimeter (see example 1) and pictures were taken as well.
Results The picture in FIG. 2 shows the differences in color of a BB-12® batch produced in production where $NH_3$ is used for pH adjustment during fermentation and two batches produced in Pilot Plant where NaOH is used for pH adjustment during fermentation.

The picture in FIG. 3 shows the same for La-5®.

From the pictures it can be seen that there is a larges improvement on the color (less red/pink color) by changing from $NH_3$ to NaOH.

Similar positive result was identified for LGG® and TH-4™.

Conclusion

The results clearly shows that by that by using NaOH as base in stead of $NH_3$—it was possible to produce dried La-5®, LGG®, BB-12® and TH-4™ compositions formulated with sodium ascorbate, wherein the compositions were NOT developing a significant pink/red color during storage of the compositions.

REFERENCES

1. L. Kurtmann et al., "Storage stability of freeze-dried Lactobacillus acidophilus (La-5) in relation to water activity and presence of oxygen and ascorbate"; Cryobiology (2009), doi:10.1016/j.cryobiol.2008.12.001—was published on the Internet in December 2008.

The invention claimed is:

1. A method for making at least 2 kg (dry weight) of a lactic acid bacteria composition containing from 1% to 50% of ascorbate or ascorbic acid (w/w–dry matter) as an antioxidant, wherein the method comprises the following steps:
    (i) culturing the lactic acid bacteria in a fermentation bioreactor comprising at least 100 L fermentation medium under suitable fermentation conditions, wherein the pH during fermentation is controlled by the addition of a base selected from the group consisting of NaOH, KOH, $Na_2CO3$, $Na_2S$ and $Na_2O$ so as to be within a range of from pH 3 to pH 8;
    (ii) harvesting the cultured lactic acid bacteria to obtain a lactic acid bacteria concentrate;
    (iii) adding ascorbate or ascorbic acid to the lactic acid bacteria concentrate; and
    (iv) processing the ascorbate-containing or ascorbic acid-containing concentrate of step (iii) in a suitable way so as to obtain said lactic acid bacteria composition containing from 1% to 50% of ascorbate or ascorbic acid (w/w–dry matter) therein, whereby the lactic acid bacteria composition develops a red/pink color at a reduced rate in comparison to a lactic acid bacteria composition in which fermentation occurs in the presence of a base comprising ammonia under the same storage condition during a storage period of 3 weeks or longer.

2. The method of claim 1, wherein the ascorbate is sodium ascorbate.

3. The method of claim 1, wherein the processing in step (iv) is drying to get a dried lactic acid bacteria composition.

4. The method of claim 1, wherein the processing in step (iv) is freezing to get a frozen lactic acid bacteria composition.

5. The method of claim 1, wherein the lactic acid bacteria are lactic acid bacteria selected from the group consisting of:
    lactic acid bacteria belonging to genus Lactobacillus comprising Lactobacillus helveticus, Lactobacillus delbruekii subsp. bulgaricus, Lactobacillus fermentum, Lactobacillus salivarius or Lactobacillus rhamnosus;
    lactic acid bacteria belonging to genus Lactococcus comprising Lactococcus lactis;
    lactic acid bacteria belonging to genus Streptococcus comprising Streptococcus thermophilus;
    lactic acid bacteria belonging to genus Leuconostoc comprising Leuconostoc lactis;
    lactic acid bacteria belonging to genus Bifidobacterium comprising Bifidobacterium longum, bifidobacterium animalis, or Bifidobacterium breve;
    lactic acid bacteria belonging to genus Propioni bacteria;
    lactic acid bacteria belonging to genus Enterococcus comprising Enterococcus faecum; and
    lactic acid bacteria belonging to genus Pediococcus.

6. The method of claim 5, wherein the lactic acid bacteria are lactic acid bacteria selected from the group consisting of:
- lactic acid bacteria belonging to genus *Lactobacillus*;
- lactic acid bacteria belonging to genus *Streptococcus*;
- lactic acid bacteria belonging to genus *Bifidobacterium*; and
- lactic acid bacteria belonging to genus *Lactococcus*.

7. The method of claim 6, wherein the lactic acid bacteria are lactic acid bacteria selected from the group consisting of *Lactobacillus acidophilus, Lactobacillus rhamnosus, Streptococcus thermophilus* and *Bifidobacterium animalis*.

8. The method of claim 3, wherein the drying in step (iv) is freeze drying to get a freeze dried lactic acid bacteria composition.

9. The method of claim 1, wherein the lactic acid bacteria composition is formulated with from 5% to 15% of ascorbate or ascorbic acid (w/w–dry matter).

10. The method of claim 1, wherein step (iii) further comprises adding a cryoprotectant.

11. The method of claim 1, wherein the fermentor (bioreactor) in step (i) contains at least 500 L fermentation medium.

12. The method of claim 3, wherein at least 5 kg (dry weight) of the dried lactic acid bacteria composition is obtained.

13. The method of claim 1, wherein the base is NaOH or KOH.

14. The method of claim 1, wherein the base is NaOH.

15. The method of claim 1, wherein the pH in step (i) is controlled so as to be within a range of from pH 4 to pH 7.

* * * * *